United States Patent [19]

Kaugars

[11] 3,932,661

[45] Jan. 13, 1976

[54] ANTHELMINTIC METHODS EMPLOYING BENZOYL CHLORIDE PHENYLHYDRAZONES

[75] Inventor: Girts Kaugars, Kalamazoo, Mich.

[73] Assignee: The Upjohn Company, Kalamazoo, Mich.

[22] Filed: Apr. 17, 1974

[21] Appl. No.: 461,705

Related U.S. Application Data

[63] Continuation-in-part of Ser. No. 67,220, Aug. 26, 1970, abandoned, which is a continuation-in-part of Ser. No. 779,251, Nov. 26, 1968, Pat. No. 3,879,543, which is a continuation-in-part of Ser. No. 709,943, March 4, 1968, abandoned.

[52] U.S. Cl. .................... 424/327; 71/70; 260/566
[51] Int. Cl.$^2$ ......................................... A61K 31/15
[58] Field of Search ................................. 424/327

[56] References Cited
UNITED STATES PATENTS 3,235,447   2/1966   Urbschat et al. .................. 424/327

OTHER PUBLICATIONS

Humphries, J., "J. Chem. Soc.," 127 (1925), pp. 1304–1307.

Primary Examiner—V. D. Turner
Attorney, Agent, or Firm—Carl A. Randles, Jr.; William G. Jameson; Roman Saliwanchik

[57] ABSTRACT

Certain benzoyl chloride phenylhydrazones have been found to be active against insects and mites, and they have also been found to be effective, broad-spectrum anthelmintics for suppressing parasitic worms in animals, particularly sheep. The benzoyl ring and the phenylhydrazone ring can be substituted with a halogen atom, a nitro group, or an alkyl group of from 1 to 6 carbon atoms, inclusive. A new class of pentahalobenzoyl chloride phenylhydrazones is described, particularly pentafluorobenzoyl chloride phenylhydrazones. The compounds are prepared by reacting a benzoic acid phenylhydrazide with phosphorus pentachloride to obtain a benzoyl chloride (dichlorophosphinyl)phenylhydrazone that is reacted with phenol to produce the desired benzoyl chloride phenylhydrazones. Certain of the compounds can be prepared by direct chlorination of a benzaldehyde phenylhydrazone. Methods of using the new compounds and new anthelmintic formulations are described. The new compound p-toluoyl chloride phenylhydrazone is effective against worms at rates at least as low as 100 mg./kg. of body weight in sheep.

9 Claims, No Drawings

ANTHELMINTIC METHODS EMPLOYING BENZOYL CHLORIDE PHENYLHYDRAZONES

CROSS REFERENCE TO RELATED APPLICATIONS

This application is a continuation-in-part of application Ser. No. 67,220 filed Aug. 26, 1970, now abandoned which application is a continuation-in-part of application Ser. No. 779,251 filed Nov. 26, 1968 now U.S. Pat. No. 3,879,543, which application is a continuation-in-part of application Ser. No. 709,943 filed Mar. 4, 1968, now abandoned.

SUMMARY OF THE INVENTION

This invention pertains to a new method of combating pestiferous insects and mites, a new method for killing and controlling (suppressing growth and reproduction of) worms (Helminths), new insecticidal and miticidal compositions, new formulations for killing and controlling worms in animals, and new chemical compounds. The invention is more particularly directed to a new method of combating insects and mites using certain benzoyl chloride phenylhydrazones, to a new method for killing and controlling parasitic worms in animals with the same, to new insecticidal and miticidal compositions comprising the certain benzoyl phenylhydrazones, to new anthelmintic formulations comprising the same, and to new pentahalobenzoyl chloride phenylhydrazones. The certain anthelmintic, insecticidal and miticidal benzoyl chloride phenylhydrazones of this invention have the general structural formula:

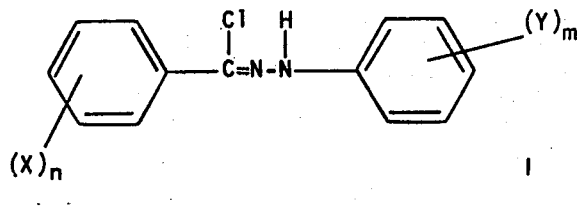

I wherein X is halogen, nitro, and alkyl of from 1 to 6 carbon atoms, inclusive; Y is alkyl of from 1 to 6 carbon atoms, inclusive, halogen, and nitro; $n$ is an integer from 0 to 5, inclusive; and $m$ is an integer from 0 to 3, inclusive; the sum of $n+m$ being not more than 6, the sum of carbon atoms in alkyl substituents being not more than 15, and there may be no more than one nitro group in the molecule.

DETAILED DESCRIPTION OF THE INVENTION

Among the benzoyl chloride phenylhydrazones of Formula 1, the specific compounds benzoyl chloride phenylhydrazone itself, p-chlorobenzoyl chloride phenylhydrazone, benzoyl chloride (p-nitrophenyl)hydrazone, p-chlorobenzoyl chloride (p-bromophenyl)hydrazone, benzoyl chloride (p-chlorophenyl)-hydrazone, and benzoyl chloride (2,4,6-trichlorophenyl)hydrazone are known. Benzoyl chloride (2,4-dinitrophenyl)-hydrazone is also a known compound, but it is relatively inactive in comparison with the other known benzoyl chloride phenylhydrazones and the new benzoyl chloride phenylhydrazones of this invention.

On embodiment of this invention involves new pentahalobenzoyl chloride phenylhydrazones having the general structural formula:

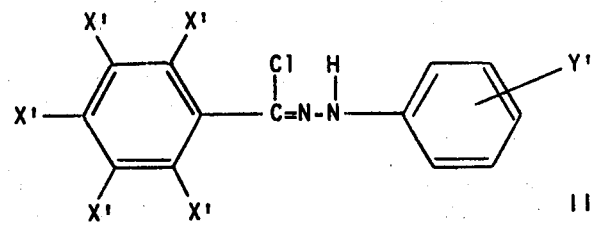

II wherein X' is halogen and Y' is hydrogen, alkyl of from 1 to 6 carbon atoms, inclusive, halogen, or nitro. Surprisingly, these new pentahalobenzoyl chloride phenylhydrazones are effective anthelmintic, insecticidal, and miticidal agents like the above-named, effective, known compounds. Particularly surprising is the fact that pentafluorobenzoyl chloride phenylhydrazone is an outstanding insecticidal and miticidal agent.

The anthelmintic, insecticidal, and miticidal benzoyl chloride phenylhydrazones of this invention are readily prepared by reacting a selected benzoic acid phenylhydrazide with phosphorus pentachloride, reacting the resulting, corresponding benzoyl chloride (dichlorophosphinyl)phenylhydrazone with phenol, and recovering the desired benzoyl chloride phenylhydrazone. The process can be represented as follows:

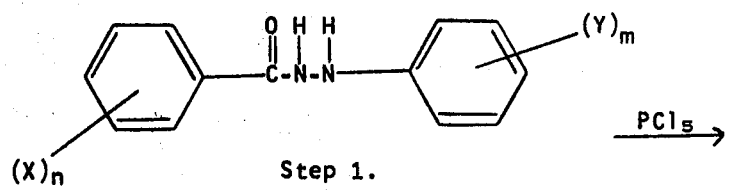

Step 1.

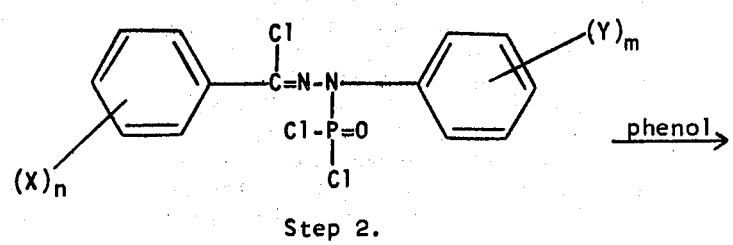

Step 2.

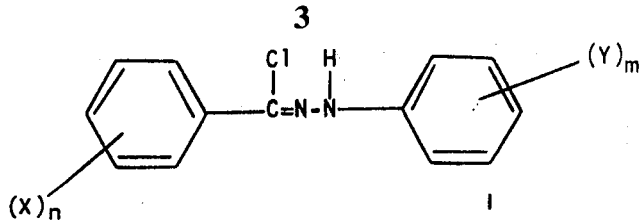

Step 1. of the foregoing process proceeds when the benzoic acid phenylhydrazide starting compound and the phosphorus pentachloride are mixed in the presence of a reaction medium at a temperature in the range of about 10°C. up to about the boiling point of the reaction medium, although higher and lower temperatures can be used. The reaction rate will be decreased at low temperatures, and a pressure vessel would be needed to effect reaction temperatures above the boiling point at atmospheric pressure. In accordance with a preferred embodiment, the initial reaction mixture is heated.

Appropriate reaction media include, for example, the chlorinated hydrocarbon solvents, alliphatic or aromatic hydrocarbon solvents, and ethers. Representative specific ones are carbon tetrachloride (preferred), methylene chloride, chloroform, 1,2-dichloroethylene, bezene, toluene, technical hexane, diethyl ether, and dioxane.

The process can be practiced without isolating the benzoyl chloride (dichlorophosphinyl)phenylhydrazone intermediate when three equivalents or more of phenol are added to the initial reaction mixture after it has been cooled to about 0° to 25°C. The phenol reacts with the benzoyl chloride (dichlorophosphinyl)phenylhydrazone intermediate to produce triphenyl phosphate, and the desired benzoyl chloride phenylhydrazone is then recovered and purified by conventional methods. The solvent medium is removed by, e.g., evaporation, and then by mechanically separating the product, e.g., filtration from the residual triphenyl phosphate or by chromatographic techniques. The compound is purified by recrystallization.

The benzoic acid phenylhydrazide starting compounds are known or can be readily prepared by known methods. According to one method a benzoyl chloride is reacted with a phenylhydrazine as described by J. Hausknecht, Chem. Ber. 22, p. 324 (1889), and E. Bamberger and W. Pemsel, Chem. Ber. 36, p. 359 (1903). Another method is described in U.S. Pat. No. 2,912,461, issued Nov. 10, 1959, that utilizes a benzoate ester and a phenylhydrazine. Still another method described by W. Autenrieth and G. Thomae, Chem Ber. 57, p. 423 (1924) reacts a benzoic acid anhydride with a phenylhydrazine to produce the corresponding benzoic acid phenylhydrazide. Preparations I through XVIII hereinafter illustrate conventional metthods for making benzoic acid phenylhydrazide starting compounds.

The anthelmintic, insecticidal, and miticidal benzoyl chloride phenylhydrazones of this invention (compounds according to Formula I) can also be prepared by chlorinating a benzaldehyde phenylhydrazone. Chlorination of a benzaldehyde phenylhydrazone can be accomplished as described by J. E. Humphries, H. Humble and R. Evans, J. Chem. Soc. 127, p. 1304 (1925). But chlorination is of limited usefulness when the starting benzaldehyde phenylhydrazone has unsubstituted active sites that will yield to chlorination at positions on the phenylhydrazone nucleus that might want to be avoided in a particular instance. Direct chlorination of benzaldehyde phenylhydrazone is an effective way of producing benzoyl chloride (2,4,6-trichlorophenyl)hydrazone.

Still another method described by L. A. Jones, C. K. Hancock, and R. B. Seligman, J. Org. Chem. 26, p. 228 (1961) can be used. The described method utilized α, α, α-trichlorotoluene and 2,4-dinitrophenylhydrazine to produce benzoyl chloride (2,4-dinitrophenyl)hydrazone. Active compounds of this invention can be prepared in the same manner.

PREPARATION I 3,4-Dichlorobenzoic acid phenylhydrazide

A mixture consisting of 71.8 g. (0.35 mole) methyl 3,4-dichlorobenzoate, 37.9 g. (0.35 mole) phenylhydrazine, 21.6 g. (0.40 mole) sodium methoxide, and 175 ml. methanol was heated at the reflux temperature for 22 hrs. After cooling the reaction mixture to about 25°C., it was poured into 500 ml. water. The aqueous mixture was filtered and the solids that collected on the filter were dissolved in 500 ml. ethanol. Refrigeration caused crystals to form which were recovered by filtration. There was thus obtained 3,4-dichlorobenzoic acid phenylhydrazide melting at 169° to 172°C. An analytical sample melting at 171.5° to 173° C. was obtained by recrystallization from ethanol.

Analysis: Calc'd. for $C_{13}H_{10}Cl_2N_2O$: C, 55.53; H, 3.59; Cl, 25.22; N, 9.97. Found: C, 55.87; H, 3.82; Cl, 25.10; N, 9.85.

PREPARATION II

Benzoic acid (2,5-dichlorophenyl)hydrazide

A mixture consisting of 17.7 g. (0.10 mole) 2,5-dichlorophenylhydrazine, 100 ml. benzene, and 22.6 g. (0.10 mole) benzoic anhydride was heated at the reflux temperature for 1 1/2 hrs. After cooling the reaction mixture to about 25°C., it was filtered. The filtrate was evaporated to dryness, and the residue was combined with solids on the filter before dispersing the solids in 700 ml. water basified with 50% aqueous sodium hydroxide to slight alkalinity. The thus washed solids were recovered on a filter, washed with more water, and recrystallized from 225 ml. 95% ethanol. There was thus obtained 23.1 g. (82.2% yield) benzoic acid (2,5-dichlorophenyl)hydrazide having a melting point of 160.5° to 161.5°C. An analytical sample melting at 161° to 162°C. was obtained by recrystallization from 95% ethanol.

Analysis Calc'd. for $C_{13}H_{10}Cl_2N_2O$: C, 55.53; H, 3.59; Cl, 25.22; N, 9.97. Found: C, 55.57; H, 3.91; Cl, 25.41; N, 10.07.

PREPARATION III p-Fluorobenzoic acid phenylhydrazide

A mixture consisting of 101.2 g. (0.602 mole) ethyl p-fluorobenzoate, 250 ml. methanol, 70.0 g. (0.646 mole) phenylhydrazine, and 33.6 g. (0.621 mole) sodium methoxide (mixed in that order) was heated at the reflux temperature for 16 hrs. After cooling the reaction mixture to about 25°C it was poured into 1500 ml. water. The aqueous mixture was filtered, and the filter cake was washed with water and recrystallized from 95% aqueous ethanol. The crystals melted at 174° to 178°C. An analytical sample of p-fluorobenzoic acid phenylhydrazide melting at 177° to 179°C. was obtained by recrystallizing once from a mixture of ethyl acetate and Skellysolve B (essentially a mixture of isomeric hexanes boiling in the range of 146° to 156°F.), and once from 75% aqueous ethanol.

Analysis: Calc'd. for $C_{13}H_{11}FN_2O$: C, 67.81; H, 4.82; N, 12.17. Found: C, 68.28; H, 5.00; N, 12.02.

PREPARATION IV p-Chlorobenzoic acid (p-bromophenyl)hydrazide

A mixture consisting of 44.7 g. (0.20 mole) p-bromophenylhydrazine hydrochloride, 250 ml. diethyl ether, 70 ml. (0.504 mole) triethylamine, and 35.0 g. (0.20 mole) p-chlorobenzoyl chloride in 50 ml. diethyl ether (mixed in that order at −5° to −15°C. during 20 minutes) was stirred continuously for about 16 hrs. at about 25° C. The reaction mixture was filtered, and the solids on the filter were washed with water and then recrystallized from 95% ethanol. There was thus obtained 15.5 g. p-chlorobenzoic acid (p-bromophenyl)hydrazide having a melting point of 185° C. (dec.). An analytical sample melting at 184.5°C. (dec.) was obtained after two recrystallizations from ethyl acetate.

Analysis: Calc'd. for $C_{13}H_{10}BrClN_2O$: C, 47.95; H, 3.10; Br, 24.54; Cl, 10.89; N, 8.61. Found: C, 48.09; H, 3.20; Br, 24.40; Cl, 10.44; N, 8.56.

PREPARATION V m-Chlorobenzoic acid phenylhydrazide

To a solution of 21.63 g. (0.20 mole) phenylhydrazine in 250 ml. diethyl ether was added 125 ml. (0.20 mole) butyl lithium (1.6M in hexane). The addition was effected at −60° to −70° C. The resulting suspension was warmed to 20° C. and 35.0 g. (0.20 mole) m-chlorobenzoyl chloride in 35 ml. ether was added dropwise. This reaction mixture was stirred at room temperature for ½ hr. and the ether was decanted. The ether was removed by evaporation, and the residue was combined with the semi-solid left by the decantation. The combined solids were dispersed in 200 ml. ethanol and 200 ml. water was added. The thus washed solids were collected on a filter, washed with water and dried. The dried solids were recrystallized from 400 ml. of a mixture of Skellysolve B and benzene (1:1) to give 19.0 g. m-chlorobenzoic acid phenylhydrazide melting at 152° to 156°C. An analytical sample having a melting point at 156° to 157.5°C. was obtained by a recrystallization from a mixture of benzene and ethanol (about 100:1) and a final recrystallization from benzene.

Analysis: Calc'd. for $C_{13}H_{11}ClN_2O$: C, 63.29; H, 4.50; Cl, 14.37; N, 11.36. Found: C, 63.34; H, 4.41; Cl, 14.35; N, 11.55.

PREPARATION VI o-Chlorobenzoic acid phenylhydrazide

Following the procedure of Preparation I, but substituting methyl 3,4-dichlorobenzoate with methyl o-chlorobenzoate, there was prepared o-chlorobenzoic acid phenylhydrazide having a melting point of 154.5° to 155.5° C.

Analysis: Calc'd. for $C_{13}H_{11}ClN_2O$: C, 63.29; H, 4.50; Cl, 14.37; N, 11.36. Found: C, 63.60; H, 4.59; Cl, 14.50; N, 11.19.

PREPARATION VII p-Isopropylbenzoic acid phenylhydrazide

To a solution of 35.0 g. (0.323 mole) phenylhydrazine in 300 ml. pyridine, cooled to about 5° to 8° C., was added 54.8 g. (0.30 mole) p-isopropylbenzoyl chloride. This reaction mixture was set aside for 37 hrs. at about 25° C. The mixture was then poured into 1500ml. ice-water and the solids that separated were collected on a filter and washed with water. After recrystallization from 850 ml. ethanol, there was obtained 64.7 g. (84.8% yield) of p-isopropylbenzoic acid phenylhydrazide melting at 198° to 201° C. An analytical sample melting at 200.5° to 202.5° C. was obtained after two recrystallizations from ethanol.

Analysis: Calc'd. for $C_{16}H_{18}N_2O$: C, 75.56; H, 7.13; N, 11.02. Found: C, 75.59; H, 7.14; N, 10.78.

PREPARATION VIII

Benzoic acid o-tolylhydrazide

To 31.73 g. (0.20 mole) of o-tolylhydrazine hydrochloride and 45.25 g. (0.20 mole) of benzoic anhydride in 250 ml. of benzene was added 35.0 ml. (0.25 mole) of triethylamine, and the suspension was refluxed for one hour. After cooling to about 25° C., the solids were filtered. The filtrate was evaporated to dryness and the residue was combined with solids on the filter before dispersing the solids in water basified with 50% aqueous sodium hydroxide to slight alkalinity. The thus washed solids were recovered on a filter, washed with more water, and recrystallized from 400 ml. of about 1:1 ethyl acetate-ethanol. There was thus obtained 30.0 g. (64.4% yield of benzoic acid o-tolylhydrazide having a melting point of 180° to 183° C. An analytical sample melting at 183° to 184.5° C. was obtained by recrystallization from ethanol and then from ethyl acetate.

Analysis: Calc'd. for $C_{14}H_{14}N_2O$: C, 74.31; H, 6.24; N, 12.38. Found: C, 74.22; H, 6.18; N, 12.66.

PREPARATION IX 2,4-Dichlorobenzoic acid phenylhydrazide

Following the procedure of Preparation VII, but substituting 2,4-dichlorobenzoyl chloride for p-isopropylbenzoyl chloride, there was prepared 2,4-dichlorobenzoic acid phenylhydrazide having a melting point of 181° to 182°C.

Analysis: Calc'd. for $C_{13}H_{10}Cl_2N_2O$: C, 55.53; H, 3.59; Cl, 25.22; N, 9.97. Found: C, 55.96; H, 3.85; Cl, 25.19; N, 978.

PREPARATION X m-Toluic acid phenylhydrazide

Following the procedure of Preparation VII, but substituting m-toluoyl chloride for p-isopropylbenzoyl chloride, there was prepared m-toluic acid phenylhydrazide having a melting point of 162° to 163° C.

Analysis: Calc'd. for $C_{14}H_{14}N_2O$: C, 74.31; H, 6.24; N, 12.28. Found: C, 74.36; H, 6.21; N, 12.53.

PREPARATION XI

Benzoic acid (p-chlorophenyl)hydrazide

Following the procedure of Preparation VIII, but substituting p-chlorophenylhydrazine hydrochloride for o-tolylhydrazine hydrochloride, there was prepared benzoic acid (p-chlorophenyl)hydrazide having a melting point of 153.5° to 154.5° C.

Analysis: Calc'd. for $C_{13}H_{11}ClN_2O$: C, 63.29; H, 4.50; Cl, 14.37; N, 11.36. Found: C, 63.03; H, 4.63; Cl, 14.16; N, 11.26.

PREPARATION XII p-Iodobenzoic acid phenylhydrazide

A solution of 44.7 g. (0.168 mole) of p-iodobenzoyl chloride in 100 ml. of dioxane was added to 18.2 g. (0.168 mole) of phenylhydrazine dissolved in 250 ml. of pyridine at 5° to 15° C. The resulting suspension was stirred at 25° C. for 3 days, poured into 2 liters of water, the solids were filtered and washed with water, dilute aqueous hydrochloric acid and then again with water. The product thus obtained was crystallized from ethanol to give 40.0 g. (70.9% yield) of p-iodobenzoic acid phenylhydrazide having a melting point of 210° to 211° C.

Analysis: Calc'd. for $C_{13}H_{11}IN_2O$: C, 46.17; H, 3.28; I, 37.53; N, 8.29. Found: C, 46.34; H, 3.44; I, 37.53; N, 8.32.

PREPARATION XIII 3,5-Dimethylbenzoic acid phenylhydrazide

Following the procedure of Preparation VII, but substituting 3,5-dimethylbenzoyl chloride for p-isopropylbenzoyl chloride, there was prepared 3,5-dimethylbenzoic acid phenylhydrazide having a melting point of 197.5° to 198.5°C.

Analysis: Calc'd. for $C_{15}H_{16}N_2O$: C, 74.97; H, 6.71; N, 11.66. Found: C, 74.92; H, 6.63; N, 11.59.

PREPARATION XIV

3-Methyl-4-nitrobenzoic acid phenylhydrazide

Following the procedure of Preparation XII, but substituting 3-methyl-4-nitrobenzoyl chloride for p-iodobenzoyl chloride, there was prepared 3-methyl-4-nitrobenzoic acid phenylhydrazide having a melting point of 163° to 164.5° C.

Analysis: Calc'd. for $C_{14}H_{13}N_3O_3$: C, 61.98; H, 4.83; N, 15.49. Found: C, 61.46; H, 4.90; N, 15.52.

PREPARATION XV 2,5-Dimethylbenzoic acid phenylhydrazide

Following the procedure of Preparation VII, but substituting 2,5-dimethylbenzoyl chloride for p-isopropylbenzoyl chloride, there was prepared 2,5-dimethylbenzoic acid phenylhydrazide having a melting point of 208° to 209° C.

Analysis: Calc'd. for $C_{15}H_{16}N_2O$: C, 74.97; H, 6.71; N, 11.66. Found: C, 74.56; H, 6.66; N, 11.56.

PREPARATION XVI

2-Chloro-4-nitrobenzoic acid phenylhydrazide

Following the procedure of Preparation XII, but substituting 2-chloro-4-nitrobenzoyl chloride for p-iodobenzoyl chloride, there was prepared 2-chloro-4-nitrobenzoic acid phenylhydrazide having a melting point of 179° to 180° C.

Analysis: Calc'd. for $C_{13}H_{10}ClN_3O_3$: C, 53.53; H, 3.45; Cl, 12.15; N, 14.41. Found: C, 53.46; H, 3.60; Cl, 12.00; N, 14.05.

PREPARATION XVII

Pentafluorobenzoic acid phenylhydrazide

Following the procedure of Preparation VII but substituting pentafluorobenzoyl chloride for p-isopropylbenzoyl chloride, there was prepared pentafluorobenzoic acid phenylhydrazide having a melting point of 152.5° to 153.5°C.

Analysis: Calc'd. for $C_{13}H_7F_5N_2O$: C, 51.66; H, 2.34; N, 9.27. Found: C, 51.84; H, 2.43; N, 9.27.

PREPARATION XVIII p-Bromobenzoic acid phenylhydrazide

Following the procedure of Preparation XII, but substituting p-bromobenzoyl chloride for p-iodobenzoyl chloride, there was prepared p-bromobenzoic acid phenylhydrazide having a melting point of 200° to 201° C.

Analysis: Calc'd. for $C_{13}H_{11}BrN_2O$: C, 53.63; H, 3.81; Br, 27.45; N, 9.62. Found: C, 53.71; H, 3.85; Br, 27.37; N, 9.80.

The following examples are illustrative of the process and products of the present invention, but are not to be construed as limiting.

EXAMPLE 1

Preparation of p-nitrobenzoyl chloride phenylhydrazone

A quantity (12.86 g., 0.05 mole) of p-nitrobenzoic acid phenylhydrazide, prepared according to the method described by J. Hausknecht, Chem. Ber. 22, p. 324 (1889), was added to a suspension of 10.41 g. (0.05 mole) phosphorus pentachloride in 75 ml. carbon tetrachloride, and the resulting suspension was heated to the reflux temperature. Heating at the reflux temperature was continued until evolution of hydrogen chloride gas ceased. After cooling the reaction mixture to about 25° C., it was poured into an ice-cold suspension of 15.5 g. (0.17 mole) of phenol in 50 ml. carbon tetrachloride. When the reaction between the phenol and the p-nitrobenzoyl chloride (dichlorophosphinyl)-phenylhydrazone intermediate was completed, the carbon tetrachloride solvent and other volatile components were removed by evaporation under reduced pressure at 30° C. The resulting suspension of p-nitrobenzoyl chloride phenylhydrazone in triphenyl phosphate was filtered and the filter cake comprising the p-nitrobenzoyl chloride phenylhydrazone was washed with 100 ml. carbon tetrachloride, 50 ml. methanol, and 50 ml. ether. The solid on the filter was recrystallized from a solvent mixture consisting of 100 ml. benzene and 300 ml. naphtha (boiling range 203° to 212°

F.). There was thus obtained 4.10 g. of p-nitrobenzoyl chloride phenylhydrazone having a melting point of 156° to 157.5° C. A second recrystallization from a mixture of benzene and Skellysolve C gave the compound melting at 157° to 158.5°C.

Analysis: Calc'd. for $C_{13}H_{10}ClN_3O_2$: C, 56.63; H, 3.66; Cl, 12.86; N, 15.24. Found: C, 56.40; H, 3.43; Cl, 13.18; N, 14.81.

EXAMPLE 2

Preparation of 3,4-dichlorobenzoyl chloride phenylhydrazone

Following the same procedure as Example 1, but substituting 28.11 g. (0.10 mole) 3,4-dichlorobenzoic acid phenylhydrazide (prepared as in Preparation I, above) for the p-nitrobenzoic acid phenylhydrazide, and using 20.83 g. (0.10 mole) phosphorus pentachloride in 100 ml. carbon tetrachloride, there was obtained 3,4-dichlorobenzoyl chloride (dichlorophosphinyl)phenylhydrazone which was reacted with 33.0 g. (0.362 mole) phenol to produce 19.45 g. (64.7% yield) of 3,4-dichlorobenzoyl chloride phenylhydrazone melting at 121° to 123.5°C. The compound recrystallized from a mixture of benzene and Skellysolve B melted at 122° to 123.5° C.

Analysis: Calc'd. for $C_{13}H_9Cl_3N_2$: C, 52.12; H, 3.03; Cl, 35.50; N, 9.35. Found: C, 52.38; H, 3.07; Cl, 35.96; N, 9.02.

EXAMPLE 3

Preparation of benzoyl chloride (2,5-dichlorophenyl)hydrazone

A quantity (16.87 g., 0.06 mole) benzoic acid (2,5-dichlorophenyl)hydrazide (Preparation II, above) was added to a solution of 12.50 g. (0.06 mole) phosphorous pentachloride in 50 ml. carbon tetrachloride, and the resulting suspension was allowed to react at 25°C. until evolution of hydrogen chloride gas slowed. The reaction mixture was then heated at the reflux temperature for 15 minutes, chilled in ice, and 17.8 g. (0.19 mole) phenol in 75 ml. carbon tetrachloride was added. After the reaction was completed, the carbon tetrachloride was removed by evaporation under reduced pressure at 30° to 32° C. The resulting suspension was filtered, and the filter cake was washed with 50 ml. cold methanol. Two recrystallizations from Skellysolve B gave benzoyl chloride (2,5-dichlorophenyl)hydrazone melting at 84.5° to 86° C.

Analysis: Calc'd. for $C_{13}H_9Cl_3N_2$: C, 52.12; H, 3.03; N, 9.35. Found: C, 52.59; H, 3.16; N, 9.27.

EXAMPLE 4

Preparation of p-toluoyl chloride phenylhydrazone

Following the procedure of Example 3, but substituting 22.63 g. (0.10 mole) p-toluic acid phenylhydrazide [prepared as described by Ponzio and Charrier, Gazz. chim. ital, 38(I), p. 528 (1908)] for the benzoic acid 2,5-dichlorophenylhydrazide and using 21.5 g. (0.102 mole) phosphorus pentachloride in 150 ml. carbon tetrachloride, there was obtained p-toluoyl chloride (dichlorophosphinyl)phenylhydrazone which was reacted with 32.0 g. (0.34 mole) phenol in 50 ml. carbon tetrachloride to produce p-toluoyl chloride phenylhydrazone. Two recrystallizations from a mixture of benzene and Skellysolve B gave the compound with a melting point of 133° to 134.5° C.

Analysis: Calc'd. for $C_{14}H_{13}ClN_2$: C, 68.71; H, 5.35; Cl. 14.49; N, 11.45. Found: C, 69.03; H, 5.27; Cl, 14.88; N, 11.37.

EXAMPLE 5

Preparation of p-fluorobenzoyl chloride phenylhydrazone

Following the same procedure as Example 1, but substituting 16.12 g. (0.07 mole) p-fluorobenzoic acid phenylhydrazide (Preparation III, above) for the p-nitrobenzoic acid phenylhydrazide and using 15.0 g. (0.072 mole) phosphorus pentachloride in 100 ml. carbon tetrachloride, there was obtained p-fluorobenzoyl chloride (dichlorophosphinyl)-phenylhydrazone which was reacted with 20.7 g. (0.22 mole) phenol in 50 ml. cold carbon tetrachloride to produce p-fluorobenzoyl chloride phenylhydrazone. After sublimation at 85°C. and 0.03 mm. mercury pressure, the compound had a melting point of 118° to 120° C.

Analysis: Calc'd. for $C_{13}H_{10}ClFN_2$: C, 62.78; H, 4.05; Cl, 14.26; F, 7.64; N, 11.27. Found: C, 62.78; H, 4.05; Cl, 14.01; F, 7.38; N, 10.87.

EXAMPLE 6

Preparation of p-chlorobenzoyl chloride (p-bromophenyl)hydrazone

A quantity (5.50 g., 0.0264 mole) phosphorus pentachloride was added to a suspension of 8.14 g. (0.0250 mole) p-chlorobenzoic acid (p-bromophenyl)hydrazide (Preparation IV, above) in 50 ml. carbon tetrachloride and the mixture was heated at the reflux temperature until evolution of hydrogen chloride gas ceased. After cooling the reaction mixture in ice, 8.0 g. (0.085 mole) phenol in 25 ml. carbon tetrachloride was added. After the reaction was completed and evolution of hydrogen chloride gas had ceased, the mixture was filtered and the filter cake was washed with 30 ml. Skellysolve B. The solids on the filter were dissolved in 20 ml. ethyl acetate, and the solution was brought to a volume of 90 ml. by the addition of Skellysolve B. The diluted solution was filtered and set aside to crystallize. There was thus obtained 5.50 g. (64.0% yield) of p-chlorobenzoyl chloride (p-bromophenyl) hydrazone having a melting point of 142° to 143.5°C.

Analysis: Calc'd. for $C_{13}H_9BrCl_2N_2$: C, 45.38; H, 2.64; Br, 23.23; Cl, 20.61; N, 8.14. Found: C, 45.37; H, 2.82; Br, 23.39; Cl, 20.56; N, 8.43.

EXAMPLE 7

Preparation of p-chlorobenzoyl chloride (2,4,6-trichlorophenyl)hydrazone

To a suspension of 6.92 g. (0.030 mole) of p-chlorobenzaldehyde phenylhydrazone in 100 ml. glacial acetic acid was added 7.0 ml. (0.154 mole) chlorine. The mixture was diluted with another 100 ml. glacial acetic acid. A heat generating reaction increased the temperature of the mixture to 45°3C. After cooling to 20°C., the mixture was filtered. The filter cake was recrystallized from Skelly-solve B to give 8.13 g. (73.6% yield) of p-chlorobenzoyl chloride (2,4,6-trichlorophenyl)hydrazone having a melting point of 122.5° to 124.5°C. An analytical sample having a melting point of 123° to 124°C was obtained by two recrystallizations from a mixture of Skellysolve B and benzene.

Analysis: Calc'd. for $C_{13}H_7Cl_5N_2$: C, 42.37; H, 1.91; Cl, 48.11; N, 7.60. Found: C, 42.75; H, 2.21; Cl, 48.15; N, 7.60.

EXAMPLE 8

Preparation of benzoyl chloride (2,4,6-trichlorophenyl)hydrazone

Following the procedure of Example 7, but substituting carbon tetrachloride for glacial acetic acid as solvent, substituting benzaldehyde phenylhydrazone for p-chlorobenzaldehyde phenylhydrazone, and cooling the reaction mixture in an ice path during the addition of chlorine and subsequently refluxing for one hour, there was prepared benzoyl chloride (2,4,6-trichlorophenyl)hydrazone having a melting point of 93° to 94.5°C.

Analysis: Calc'd. for $C_{13}H_8Cl_4N_2$: C, 46.74; H, 2.41; Cl, 42.46; N, 8.39. Found: C, 47.03; H, 2.34; Cl, 42.10; N, 8.22.

EXAMPLE 9

Preparation of m-chlorobenzoyl chloride phenylhydrazone

Following the procedure of Example 1, but substituting m-chlorobenzoic acid phenylhydrazide (Preparation V, above) for p-nitrobenzoic acid phenylhydrazide, there was prepared m-chlorobenzoyl chloride phenylhydrazone having a melting point of 80° to 81.5°C.

Analysis: Calc'd. for $C_{13}H_{10}Cl_2N_2$: C, 58.89; H, 3.80; Cl, 26.74; N, 10.57. Found: C, 59.40; H, 4.00; Cl, 26.75; N, 10.57.

EXAMPLE 10

Preparation of p-isopropylbenzoyl chloride phenylhydrazone

Following the procedure of Example 1, but substituting p-isopropylbenzoic acid phenylhydrazide (Preparation VII, above) for p-nitrobenzoic acid phenylhydrazide, there was prepared p-isopropylbenzoyl chloride phenylhydrazone having a melting point of 100.5° to 102°C.

Analysis: Calc'd. for $C_{16}H_{17}ClN_2$: C, 70.45; H, 6.28; Cl, 13.00; N, 10.27. Found: C, 70.59; H, 6.39; Cl, 13.00; N, 9.80.

EXAMPLE 11

Preparation of o-toluoyl chloride phenylhydrazone

Following the procedure of Example 13, below, but substituting o-toluic acid phenylhydrazide for o-chlorobenzoic acid phenylhydrazide, there was prepared o-toluoyl chloride phenylhydrazone.

EXAMPLE 12

Preparation of 2,4-dichlorobenzoyl chloride phenylhydrazone

Following the procedure of Example 1, but substituting 2,4-dichlorobenzoic acid phenylhydrazide (Preparation IX, above) for p-nitrobenzoic acid phenylhydrazide, there was prepared 2,4-dichlorobenzoyl chloride phenylhydrazone having a melting point of 88.5° to 89.5°C.

Analysis: Calc'd. for $C_{13}H_9Cl_3N_2$: C, 52.12; H, 3.03; Cl, 35.50; N, 9.35. Found: C, 52.29; H, 3.06; Cl, 35.69; N, 8.90.

EXAMPLE 13

Preparation of o-chlorobenzoyl chloride phenylhydrazone

Following the procedure of Example 1, but substituting o-chlorobenzoic acid phenylhydrazide (Preparation VI, above) for p-nitrobenzoic acid phenylhydrazide, there was prepared o-chlorobenzoyl chloride phenylhydrazone in the form of an oil. The compound was purified by column chromatography on silica gel using an eluting solvent consisting of one part Skellysolve B and one part benzene.

Analysis: Calc'd. for $C_{13}H_{10}Cl_2N_2$: C, 58.89; H, 3.80; Cl, 26.74; N, 10.57. Found: C, 58.68; H, 3.87; Cl, 26.50; N, 10.05.

EXAMPLE 14

Preparation of benzoyl chloride o-tolylhydrazone

Following the procedure of Example 13, but substituting benzoic acid o-tolyhydrazide (Preparation VIII, above) for o-chlorobenzoic acid phenylhydrazide, there was prepared benzoyl chloride o-tolylhydrazone having a melting point of 64.5° to 66°C.

Analysis: Calc'd. for $C_{14}H_{13}ClN_2$: C, 68.71; H, 5.35; Cl, 14.49; N, 11.45. Found: C, 69.06; H, 5.42; Cl, 14.61; N, 11.22.

EXAMPLE 15

Preparation of m-toluoyl chloride phenylhydrazone

Following the procedure of Example 13, but substituting m-toluic acid phenylhydrazide (Preparation X, above) for o-chlorobenzoic acid phenylhydrazide, there was prepared m-toluoyl chloride phenylhydrazone having a melting point of 66° to 67°C.

Analysis: Calc'd. for $C_{14}H_{13}ClN_2$: C, 68.71; H, 5.35; Cl, 14.49; N, 11.45. Found: C, 68.84; H, 5.41; Cl, 14.45; N, 11.17.

EXAMPLE 16

Preparation of benzoyl chloride (p-chlorophenyl)hydrazone

Following the procedure of Example 1, but substituting benzoic acid (p-chlorophenyl)hydrazide (Preparation XI, above) for p-nitrobenzoic acid phenylhydrazide, there was prepared benzoyl chloride (p-chlorophenyl)hydrazone having a melting point of 107° to 108.5°C.

Analysis: Calc'd. for $C_{13}H_{10}Cl_2N_2$: C, 58.89; H, 3.80; Cl, 26.74; N, 10.57. Found: C, 59.11; H, 3.88; Cl, 26.62; N, 10.10.

EXAMPLE 17

Preparation of p-bromobenzoyl chloride phenylhydrazone

Following the procedure of Example 1, but substituting p-bromobenzoic acid phenylhydrazide (Preparation XVIII, above) for p-nitrobenzoic acid phenylhydrazide, there was prepared p-bromobenzoyl chloride phenylhydrazone having a melting point of 151.5° to 153°C.

Analysis: Calc'd. for $C_{13}H_{10}BrClN_2$: C, 50.43; H, 3.26; Br, 25.81; Cl, 11.45; N, 9.05. Found: C, 50.05; H, 3.23; Br, 25.77; Cl, 11.70; N, 9.16.

EXAMPLE 18

Preparation of benzoyl chloride (p-nitrophenyl)-hydrazone

Following the procedure of Example 1, but substituting benzoic acid (p-nitrophenyl)hydrazide [prepared as described by Hyde, Chem. Ber. 32, p. 1810 (1899)] for p-nitrobenzoic acid phenylhydrazide, there was prepared benzoyl chloride (p-nitrophenyl)hydrazone having a melting point of 195° to 196°C.

Analysis: Calc'd. for $C_{13}H_{10}ClN_3O_2$: C, 56.63; H, 3.66; Cl, 12.86; N, 15.24. Found: C, 56.76; H, 3.73; Cl, 12.90; N, 15.37.

EXAMPLE 19

Preparation of benzoyl chloride (2,4-dibromophenyl)hydrazone

To an ice-cold solution of 5.00 g. (0.0217 mole) of benzoyl chloride phenylhydrazone in 200 ml. of carbon tetrachloride was added 10.8 g. (0.0675 mole) of bromine dissolved in 25 ml. of carbon tetrachloride. The solution was subsequently refluxed for 4 hours. The solvent was removed by evaporation under reduced pressure, and the residual solid was recrystallized from Skellysolve B. The crystals melted at 103° to 104°C. An analytical sample of benzoyl chloride 2,4-(dibromophenyl)hydrazone having a melting point of 106° to 107°C was obtained by recrystallizing twice from Skellysolve B.

Analysis: Calc'd. for $C_{13}H_9Br_2ClN_2$: C, 40.19; H, 2.33; N, 7.21. Found: C, 39.50; H, 2.46; N, 7.16.

EXAMPLE 20

Preparation of 2,5-dimethylbenzoyl chloride phenylhydrazone

Following the procedure of Example 13, but substituting 2,5-dimethylbenzoic acid phenylhydrazide (Preparation XV, above) for o-chlorobenzoic acid phenylhydrazide, there was prepared 2,5-dimethylbenzoyl chloride phenylhydrazone having a melting point of 48.5° to 49°C.

Analysis: Calc'd. for $C_{15}H_{15}ClN_2$: C, 69.62; H, 5.84; Cl, 13.70; N, 10.83. Found: C, 69.15; H, 5.81; Cl, 13.90; N, 10.66.

EXAMPLE 21

Preparation of 2-chloro-4-nitrobenzoyl chloride phenylhydrazone

Following the procedure of Example 1, but substituting 2-chloro-4-nitrobenzoic acid phenylhydrazide (Preparation XVI, above) for p-nitrobenzoic acid phenylhydrazide, there was prepared 2-chloro-4-nitrobenzoyl chloride phenylhydrazone having a melting point of 124° to 126°C.

Analysis: Calc'd. for $C_{13}H_9Cl_2N_3O_2$: C, 50.34; H, 293; Cl, 22.86; N, 13.55. Found: C, 50.22; H, 3.15; Cl, 23.03; N, 13.29

EXAMPLE 22

Preparation of 2,6-dichlorobenzoyl chloride phenylhydrazone

Following the procedure of Example 1, but substituting 2,6-dichlorobenzoic acid phenylhydrazide for p-nitrobenzoic acid phenylhydrazide, there was prepared 2,6-dichlorobenzoyl chloride phenylhydrazone having a melting point of 95.5° to 96.5°C.

Analysis: Calc'd. for $C_{13}H_9Cl_3N_2$: Cl, 35.51; N, 9.35. Found: Cl, 35.55; N, 9.17.

EXAMPLE 23

Preparation of pentafluorobenzoyl chloride phenylhydrazone

Following the procedure of Example 1, but substituting pentafluorobenzoic acid phenylhydrazide (Preparation XVII, above) for p-nitrobenzoic acid phenylhydrazide, there was prepared pentafluorobenzoyl chloride phenylhydrazone having a melting point of 117° to 118°C.

Analysis;
Calc'd. for $C_{13}H_6ClF_5N_2$: C, 48.69; H, 1.89; Cl, 11.06; N, 8.74. Found: C, 49.03; H, 2.20; Cl, 11.04; N, 8.91.

EXAMPLE 24

Preparation of 3,4-dimethylbenzoyl chloride phenylhydrazone

Following the procedure of Example 13, but substituting 3,4-dimethylbenzoic acid phenylhydrazide for o-chlorobenzoic acid phenylhydrazide, there was prepared 3,4-dimethylbenzoyl chloride phenylhydrazone.

EXAMPLE 25

Preparation of p-iodobenzoyl chloride phenylhydrazone

Following the procedure of Example 1, but substituting p-iodobenzoic acid phenylhydrazide (Preparation XII, above for p-nitrobenzoic acid phenylhydrazide, there was prepared p-iodobenzoyl chloride phenylhydrazone having a melting point of 164° to 165°C.

Analysis: Calc'd. for $C_{13}H_{10}ClIN_2$: C, 43.78; H, 2.83; Cl, 9.94; 1, 35.59; N, 7.86. Found: C, 44.02; H, 2.94; Cl, 9.95; 1, 35.92; N, 7.93.

EXAMPLE 26

Preparation of 3-methyl-4-nitrobenzoyl chloride phenylhydrazone

Following the procedure of Example 1, but substituting 3-methyl-4-nitrobenzoic acid phenylhydrazide (Preparation XIV, above) for p-nitrobenzoic acid phenylhydrazide, there was prepared 3-methyl-4-nitrobenzoyl chloride phenylhydrazone having a melting point of 146° to 147.5°C.

Analysis: Calc'd. for $C_{14}H_{12}ClN_3O_2$: C, 58.04; H, 4.18, Cl, 12.24; N, 14.50. Found: C, 58.06; H, 4.29; Cl, 12.41; N, 14.31.

EXAMPLE 27

Preparation of 3,5-dimethylbenzoyl chloride phenylhydrazone

Following the procedure of Example 13, but substituting 3,5-dimethylbenzoic acid phenylhydrazide (Preparation XIII, above) for o-chlorobenzoic acid phenylhydrazide, there was prepared 3,5-dimethylbenzoyl chloride phenylhydrazone having a melting point of 47.5° to 48.5°C after sublimation at 65°C and 0.002 mm. mercury pressure.

Analysis: Calc'd. for $C_{15}H_{15}N_2Cl$: Cl, 13.70; N, 10.83. Found: Cl, 13.74; N, 10.92.

EXAMPLE 28

Following the procedure of Example 1, but substituting p-butylbenzoic acid phenylhydrazide, p-(1-methylbutyl)-benzoic acid phenylhydrazide, p-hexylbenzoic acid phenylhydrazide, 3,4,5-trimethylbenzoic acid phenylhydrazide, 2,4,6-triisopropylbenzoic acid (3,5-diisopropylphenyl)hydrazide, p-toluic acid (p-ethylphenyl)hydrazide, p-hexylbenzoic acid (p-hexylphenyl)hydrazide, 3-chloro-5-methylbenzoic acid phenylhydrazide, p-toluic acid (p-bromophenyl)hydrazide, p-nitrobenzoic acid (p-bromophenyl)hydrazide, p-nitrobenzoic acid (p-isopropylphenyl)hydrazide, and p-isopropylbenzoic acid (2-chloro-4-nitrophenyl)hydrazide for p-nitrobenzoic acid phenylhydrazide, there were prepared the corresponding p-butylbenzoyl chloride phenylhydrazone, p-(1-methylbutyl)-benzoyl chloride phenylhydrazone, p-hexylbenzoyl chloride phenylhydrazone, 3,4,5-trimethylbenzoyl chloride phenylhydrazone, 2,4,6-triisopropylbenzoyl chloride (3,5-diisopropylphenyl)hydrazone, p-toluoyl chloride (p-ethylphenyl)hydrazone, p-hexylbenzoyl chloride (p-hexylphenyl)hydrazone, 3-chloro-5-methylbenzoyl chloride phenylhydrazone, p-toluoyl chloride (p-bromophenyl)hydrazone, p-nitrobenzoyl chloride (p-bromophenyl)hydrazone, p-nitrobenzoyl chloride (p-isopropylphenyl)hydrazone, and p-isopropylbenzoyl chloride (2-chloro-4-nitrophenyl)hydrazone, respectively.

EXAMPLE 29

Following the procedure of Example 8, but substituting m-tolualdehyde phenylhydrazone, p-isopropylbenzaldehyde (2,4,6-trichlorophenyl)hydrazone, and benzaldehyde p-tolylhydrazone for benzaldehyde phenylhydrazone, there were prepared m-toluoyl chloride (2,4,6-trichlorophenyl)hydrazone, p-isopropylbenzoyl chloride (2,4,6-trichlorophenyl)hydrazone, and benzoyl chloride (2,6-dichloro-4-methylphenyl)-hydrazone, respectively.

EXAMPLE 30

Preparation of benzoyl chloride (2,4-dichlorophenyl)hydrazone

A suspension consisting of 6.86 g. (0.035 mole) benzaldehyde phenylhydrazone, 100 ml. glacial acetic acid, and 200 ml. carbon tetrachloride was cooled to 0°C. and 0.11 mole chlorine was introduced while the temperature of the reaction mixture was kept below 10°C. After being set aside for about 16 hrs., the reaction solution was filtered. The filtrate was concentrated by removing most of the carbon tetrachloride under reduced pressure. The concentrate was poured over crushed ice and the solids that formed were collected on a filter. The filter cake was recrystallized from glacial acetic acid to give 4.9 g. benzoyl chloride (2,4-dichlorophenyl)hydrazone having a melting point at 89.0° to 90.5°C.

Analysis: Calc'd. for $C_{13}H_9Cl_3N_2$: C, 52.12; H, 3.03; Cl, 35.50; N, 9.35. Found: C, 52.27; H, 2.99; Cl, 35.69; N, 9.68.

The anthelmintic, insecticidal, and miticidal benzoyl chloride phenylhydrazones of Formula I can be used as the pure compounds, such as those described in the Examples, as mixtures of pure compounds, or as technical grade compounds from commercial production; but for practical reasons, the compounds are preferably formulated as anthelmintic, insecticidal, and miticidal compositions. More particularly, the benzoyl chloride phenylhydrazones are preferably formulated with a diluent carrier. There are many different kinds of diluent carriers useful for preparing insecticidal and miticidal compositions. Dispersible insecticide and miticide carriers are commonly used in the art. Such carriers may or may not include adjuvants such as wetting agents, emulsifying agents, stickers, and other components that indirectly promote efficacy.

For example, pesticidal compositions useful against insects and mites which infest plants can be formulated as dusts, wettable powders, emulsifiable concentrates, aqueous dispersions, solutions, and flowable creams for application to animals and foliage, seeds or other parts of plants. Compositions suitable for root or bole infusion can be made, and granular compositions can be made and applied to soil or on surfaces. Moreover, the benzoyl chloride phenylhydrazones of the invention can be the sole active agent in a composition or other insecticidal, miticidal, fungicidal, virucidal, bactericidal, or synergistic compounds may be included.

The benzoyl chloride phenylhydrazones can be readily formulated as dusts by grinding a mixture of the compound and a pulverulent carrier in the presence of each other. Grinding is conveniently accomplished in a ball mill, a hammermill, or by air-blast micronization. A suitable ultimate particle size is less than 60 microns. Preferably, 95% of the particles are less than 50 microns, and about 75% are 5 to 20 microns. Dusts of that degree of comminution are conveniently free-flowing and can be applied to animals, inanimate matter, fruit trees, crop plants, and soil so as to effect thorough distribution and coverage. Dusts are particularly adapted for effectively controlling insects and mites over wide areas when applied by airplane. They are also indicated for application to the undersides of plant foliage and to the skin of poultry and hairy animals.

Representative suitable pulverulent carriers include the natural clays such as China, Georgia, Barden, attapulgus, kaolin, and bentonite clays; minerals in their natural forms as they are obtained from the earth such as talc, pyrophyllite, quartz, diatomaceous earth, fuller's earth, chalk, rock phosphates and sulfates, calcium carbonates, sulfur, silica and silicates; chemically modified minerals such as washed bentonite, precipitated calcium phosphate, precipitated calcium silicate, synthetic magnesium silicate, and colloidal silica; and organic flours such as wood, walnut shell, soybean, cottonseed, and tobacco flours, and freeflowing, hydrophobic starches.

Dusts can also be prepared by dissolving a benzoyl chloride phenylhydrazone in a volatile solvent such as methylene chloride, mixing the solution with a pulverulent carrier and evaporating the solvent.

The proportions of pulverulent carrier and benzoyl chloride phenylhydrazone can vary over a wide range depending upon the insects or mites to be controlled and the conditions of treatment. In general, dust formulations can contain up to about 90 percent (on a weight basis) of the active ingredient. Dusts having as little as 0.001 percent of the active ingredient can be used, but a generally preferred proportion is from about 0.50 to about 20 percent of active ingredient.

The dispersible powder formulations of this invention are prepared by incorporating a surfactant in a dust composition prepared as described above. When about 0.1 to about 12 percent of a surfactant is incorporated in a dust, the dispersible powder thus obtained is particularly adapted for further admixture with water for spraying on inanimate matter and products, fruit trees, field crops, soil, and livestock. The dispersible powders can be admixed with water to obtain any desired concentration of active ingredient, and the mixture can be applied in amounts sufficient to obtain predetermined rates of application and uniform distribution. With this flexibility in mind, the dispersible powders of the invention can conveniently comprise preferably about 10 to about 80 percent of active ingredient.

Representative surfactants useful for preparing dispersible powder formulations of this invention include alkyl sulfates and sulfonates, alkyl aryl sulfonates, sulfosuccinate esters, polyoxyethylene sulfates, polyoxyethylene-sorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. The preferred class of surfactants includes blends of sulfonated oils and polyalcohol carboxylic acid esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, and X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul N$_4$S). It will be understood, of course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1 percent or less. The dispersible powder compositions can be formulated with a mixture of surfactants of the types indicated if desired.

A suitable dispersible powder formulation is obtained by blending and milling 327 lbs. of Georgia Clay, 4.5 lbs. of isooctylphenoxy polyethoxy ethanol (Triton X-100) as a wetting agent, 9 lbs. of a polymerized sodium salt of substituted benzoid long-chain sulfonic acid (Daxad 27) as a dispersing agent, and 113 lbs. of the active ingredient. The resulting formulation has the following percentage composition (parts herein are by weight unless otherwise specified).

| | |
|---|---|
| Active ingredient | 25% |
| Isooctylphenoxy polyethoxy ethanol | 1% |
| Polymerized sodium salt of substituted benzoid long-chain sulfonic acid | 2% |
| Georgia Clay | 72% |

This formulation, when dispersed in water at the rate of 10 lbs. per 100 gals., gives a spray formulation containing about 0.3% (3000 ppm) active ingredient which can be applied to insects or mites, plants or other insect of mite habitats, or insect or mite foods to control insects or mites.

If desired, dispersants such as methylcellulose, polyvinyl alcohol, sodium ligninsulfonates, and the like can be included in the dispersible powder formulations of this invention. Adhesive or sticking agents such as vegetable oils, naturally occurring gums, casein, and others can also be included. Corrosion inhibitors such as epichlorohydrin and anti-foaming agents such as stearic acid can also be included.

The insecticidal and miticidal benzoyl chloride phenylhydrazones of this invention can be applied to insects, mites, objects, or situs in aqueous sprays without a solid carrier. Since, however, the compounds themselves are relatively insoluble in water they are preferably dissolved in a suitable inert organic solvent carrier. Advantageously, the solvent carrier is immiscible with water so that an emulsion of the solvent carrier in water can be prepared. If, for example, a water-miscible solvent carrier such as ethanol is used the solvent carrier will dissolve in the water and any excess benzoyl chloride phenylhydrazone will be thrown out of solution. In an oil-in-water emulsion, the solvent phase is dispersed in the water phase and the dispersed phase contains the active ingredient. In this way, uniform distribution of a water insoluble active ingrediant is achieved in an aqueous spray. A solvent carrier in which benzoyl chloride phenylhydrazones are highly soluble is desirable so that relatively high concentrations of active ingredient can be obtained. Sometimes, one or more solvent carriers with or without a cosolvent can be used in order to obtain concentrated solutions of the active ingredient, the main consideration being to employ a waterimmiscible solvent for the active ingredient that will hold the compound in solution over the range of concentrations useful for applying to insects and mites.

The emulsifiable concentrates of the invention are prepared, therefore, by dissolving the active ingredient and a surfactant in a substantially water-immiscible solvent carrier (i.e., a solvent carrier which is soluble in water to the extent of less than 2.5 percent by volume at temperatures of the order of 20° to 30° C.), for example, cyclohexanone, methyl propyl ketone, summer oils, ethylene dichloride, aromatic hydrocarbons such as benzene, toluene, and xylene, and high-boiling petroleum hydrocarbons such as kerosene, diesel oil, and the like. If desired, a cosolvent such as methyl ethyl ketone, acetone, isopropanol, and the like can be included with the solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed, if desired.

Advantageously, the concentration of active ingredient in the emulsifiable concentrates can range from about 5 to about 50 percent by weight, preferably from about 10 to about 40 percent. A concentrate comprising 20 percent (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Simiarly, 1 qt. of a 20 percent concentrate mixed with 40 gals. of water provides about 1200 ppm (parts per million) of active ingredient. In the same manner, more concentrated solutions of active ingredient can be prepared.

The concentrate compositions of the invention which are intended for use in the form of aqueous dispersion or emulsions can also comprise a humectant, that is to say, an agent which will delay the drying of the composition in contact with material to which it has been applied. Suitable humectants include glycerol, diethylene glycol, solubilized lignins, such as calcium ligninsulfonate, and the like.

The granular compositions of this invention are convenient for application to soil when persistence is desired. Granulars are readily applied broadcast or by localized, e.g., in-the-row applications. The individual granules may be any desired size from 30 to 60 mesh up to 20 to 40 mesh, or even larger. Granulars are prepared by dissolving the active compound in a solvent such as methylene chloride, xylene, or acetone and applying the solution to a quantity of a granulated absorbent carrier. Representative granulated absorbent carriers include ground corn cobs, ground walnut shells, ground peanut hulls, and the like. If desired, the impregnated granulated absorbent carrier can be coated with a coating that will preserve the integrity of the granular until it is applied to an object or situs favorable for release of the active ingredient.

The rates of application to insects, mites, objects, or situs will depend upon the species of insects or mites to be controlled, the presence or absence of desirable living organisms, temperature conditions of treatment, and the method and efficiency of application. In general, insecticidal and miticidal activity is obtained when the compounds are applied at concentrations of about 10 to about 6000 ppm, preferably at concentrations of about 30 to about 4000 ppm.

The compositions containing benzoyl chloride phenylhydrazones according to the invention, can be applied to insects, mites, objects or situs by conventional methods. For example, an area of soil, a building, or plants can be treated by spraying wettable powder suspensions, emulsions, or solutions from power sprayers or from hand-operated knapsack sprayers. Dips can be used for livestock. Dusts can be applied by power dusters, or by hand-operated dusters. Creams and ointment formulations can be applied to skin or objects for prolonged protection from insects or mites.

The active compounds of the invention can also be formulated in relatively dilute proportions in a dispersible insecticide carrier for household applications. Thus, the active compounds can be formulated in dusts having from about 0.1to 5.0 percent active ingredient with a dusting powder as hereinbefore described, and in solutions containing from about 0.01 to about 5.0 percent active ingredient with deodorized kerosene for aerosol applications.

It will of course be appreciated that the conditions encountered when applying the method and compositions of this invention to actual practice can vary widely. Included among the variables that may be encountered are the degree of infestation by insects or mites, the particular pest to be controlled, the particular situs being treated, the age or degree of development of animals or plants, the prevailing weather conditions, such as temperature relative humidity, rainfall, dews, and so forth.

The compounds of Formula 1 are effective pesticides that can be used to control invertebrate pests in agriculture, in industry and around the home. The compounds have been found to be active against invertebrate animals of the Phylum Arthropoda, illustratively Class Insecta, for example, order Coleoptera, more specifically, the cotton boll weevil (Anthonomus grandis Boheman), the confused flour beetle (Tribolium confusum Jacquelin de Val), and the Mexican bean beetle Epilachna varivestis Mulsant), order Diptera, more specifically the housefly (Musca donestica Linnaeus), order Orthoptera, more specifically, the house cricket (Acheta domesticus Linnaeas), and the German cockroach (Blatella germanica Linnaeus), and order Lepidoptera, more specifically, the Southern armyworm (Prodenia eridania Cramer), and Class Arachnida, for example, order Acarina, more specifically, the two-spotted spider mite (Tetranychus urticae Koch).

Efficacy against invertebrate pests has been demonstrated at concentrations of 1000, 500, 100, 50, and even 10 ppm depending upon the specific insect or mite used. Some invertebrate animal pests will be more sensitive to the compounds than others, and others might be quite resistant. In general, the compounds of Formula 1 are used at concentrations ranging from about 30 to about 6000 ppm.

Compounds of the invention have also shown activity as defoliants and against parasitic worms, e.g. Nematospiroides dubius and Syphacia obvelata. The compounds benzoyl chloride (2,5dichlorophenyl)hydrazone and p-chlorobenzoyl chloride (2,4,6-trichlorophenyl)hydrazone have been found to have anorexigenic activity.

The activity of benzoyl chloride phenylhydrazones, compounds of Formula 1, against helminths was initially observed against Nematospiroides dubius and Syphacia obvelata in mice. Illustratively, the specific compounds benzoyl chloride phenylhydrazone, and p-toluoyl chloride phenylhydrazone are effective against worms, particularly parasitic worms of animals, and more particularly helminth parasitic in ovines (sheep).

Further observations in lambs infested with Haemonchus, Ostertagia, Trichostrongylus, Nematodirus, Strongyloides, Oesophagostomum, Bunostomum, Trichuris, and/or Moniezia showed that the compounds are active at practical low dosages, and that they possess broad-spectrum activity, e.g., against both roundworms and tapeworms.

A preliminary test with lambs was effected by maintaining worm infested lambs under satisfactory environmental conditions with feed and water available ad libitum. Pretreatment fecal examinations were made in order to characterize and evaluate the parasitism of each animal. The presence of helminth ova was recorded in terms of the number of eggs per gram of feces.

On the day of treatment, each lamb was weighed and a dosage for it was calculated in terms of milligrams of compound per kilogram of body weight. The calculated dosage of compound was pulverized and packed in a gelatin capsule for oral administration.

In this preliminary test one lamb received 200 mg. p-toluoyl chloride phenylhydrazone per kilogram of body weight - a total dosage of 5.0 g. After treatment, there was significantly fewer helminth eggs in the feces, and reduced numbers of helminths at necropsy thus indicating that the 200 mg./kg. dosage was somewhat effective. Better results at even lower dosages were achieved in subsequent test.

Another lamb received 300 mg./kg. of the compound - a total dosage of 6.8 g. In this case, helminth egg counts were reduced significantly (except Trichuris) and on necropsy worm infestation was found to be low. The egg counts and observations at necropsy established activity against Haemonchus, Ostertagia, Trichostrongylus, Nematodirus, Strongyloides, and Oesophagostomum.

Still another lamb received 400 mg./kg. of the compound — a total dosage of 11.7 g. Activity against Haemonchus, Ostertagia, Trichostrongylus, Nematodirus and Strongyloides was established by significantly lowered egg counts and absence of worms at necropsy. There was lack of noticeable activity against Trichuris ovis. According to this preliminary test, the compound is established as useful for killing and controlling worms in sheep.

Further, the compound and the other compounds of the invention are contemplated as useful for killing and controlling parasitic worms in ovines, bovines, equines, porcines, aves, canines, felines, piscines and other animals.

EXAMPLE 31

A subsequent. similar, but more extensive test showed excellent activity at 100 mg. and 200 mg. per kilogram of body weight. At both dosages, the compound p-toluoyl chloride phenylhydrazone was efficacious against Haemonchus, Ostertagia, Nematodirus, Trichostrongylus, Strongyloides, Oesophagostomum, and Cooperia. At these dosages, activity against the tapeworm Moniezia was observed.

In view of the absence of signs of toxicity of the compound to the lambs, and advantageous anthelimintic agent has been discovered.

In the comprehensive test with 100 mg./kg. and 200 mg./ kg. dosages of p-toluoyl chloride phenylhydrazone, five lambs were used for each dosage level, and five lambs were maintained as unmedicated controls. Daily egg counts in the feces were made before and after treatment. The lambs were killed and examined post-mortem for worms present 11 days after treatment. Helminth populations were recovered, enumerated and identified.

The mean percentage efficacy against specific helminths in the test lambs was calculated by subtracting the average number of the helminths observed in the treated lambs, post-mortem, from the average number observed in the unmedicated controls, post-mortem; dividing the remainder by the latter average number; and multiplying by 100. Accordingly, the mean percentage efficacies against the various helminths identified in the test lambs were calculated and found to be as follows:

| Helminth | 100 mg./kg. | 200 mg./kg. |
| --- | --- | --- |
| Haemonchus | 99.9 | 99.9 |
| Ostertagia | 100 | 100 |
| Trichostrongylus | 97.3 | 100 |
| Nematodirus | 100 | 100* |
| Strongyloides | 98.4 | 100 |
| Oesophagostomum | 100 | 90.6 |
| Bunostomum | — | 96 |
| Cooperia | 100* | 100 |
| Trichuris | — | positive* |

\* = only one lamb infected
— = parasites not present

The total numbers of various helminths found in the non-medicated control lambs, post-mortem, were as follows:

Non-medicated Control Group Data-Total Number of Parasites Recovered at Necropsy

| Lamb Number | Haemonchus | Ostertagia | Trichostrongylus | Nematodirus | Strongyloides | Oesophagostomun | Bunostomum | Cooperia | Trichuris | Tapeworm |
| --- | --- | --- | --- | --- | --- | --- | --- | --- | --- | --- |
| 314 | 16 | 2 | 11 | 2 | 11 | 1 | — | — | 5 | — |
| 326 | 130 | 40 | 1110 | — | 430 | — | 50 | — | 45 | — |
| 330 | 1210 | 640 | 190 | 30 | 710 | 6 | 40 | 360 | 2 | — |
| 335 | 180 | 70 | 38 | 4 | 29 | — | — | 31 | 3 | — |
| 338 | 930 | 260 | 110 | 40 | 130 | 18 | — | 30 | 86 | — |
| Total No. of Parasites Remaining | 2466 | 1012 | 1459 | 76 | 923 | 25 | 90 | 421 | 141 | — |
| Average No. of Parasites Remaining | 493 | 202 | 292 | 19 | 185 | 8 | 45 | 140 | 28 | — |
| No. Lambs Infected At Necropsy | 5 | 5 | 5 | 4 | 5 | 3 | 2 | 3 | 5 | — |

— = no infection (or very light infection).
0 = parasitism detected as indicated by EPG data, but no parasites recovered.

The total numbers of the various helminths found in the 100 mg./kg. dosage group, post-mortem, were as follows:

Treatment at 100 mg./kg. Group Data - Total Number of Parasites Recovered at Necropsy

| Lamb Number | Haemonchus | Ostertagia | Trichostrongylus | Nematodirus | Strongyloides | Oesophagostomum | Bunostomum | Cooperia | Trichuris | Tape-Worm |
|---|---|---|---|---|---|---|---|---|---|---|
| 309 | 2 | 0 | 0 | 0 | 2 | — | — | 0 | 31 | — |
| 310 | 0 | 0 | — | — | 0 | — | — | — | 83 | — |
| 324 | 0 | 0 | 15 | 0 | 0 | — | — | — | 3 | — |
| 329 | 0 | 0 | 0 | — | 0 | 0 | — | — | 37 | — |
| 340 | 0 | 0 | 0 | — | 11 | 0 | — | 0 | 4 | — |
| Total No. of Parasites Remaining | 2 | 0 | 15 | 0 | 13 | 0 | — | 0 | 158 | — |
| Average No. of Parasites Remaining | <1 | 0 | 4 | 0 | 3 | 0 | — | 0 | 32 | — |
| %Efficacy | 99.9 | 100 | 97.3 | 100 | 98.4 | 100 | — | 100 | 0 | — |

— = no infection (or very light infection).
0 = parasitism detected as indicated by EPG data, but no parasites recovered.

The total numbers of the various helminths found in the 200 mg./kg. dosage group, post-mortem, were as follows:

Treatment at 200 mg./kg. Group Data - Total Number of Parasites Recovered at Necropsy

| Lamb Number | Haemonchus | Ostertagia | Trichostrongylus | Nematodirus | Strongyloides | Oesophagostomum | Bunostomum | Cooperia | Trichuris | Tape-Worm |
|---|---|---|---|---|---|---|---|---|---|---|
| 305 | 0 | 0 | 0 | — | 0 | — | 2 | — | 6 | — |
| 316 | 0 | 0 | 0 | — | 0 | 0 | — | — | 64 | — |
| 321 | 1 | 0 | 0 | — | 0 | 0 | 1 | — | 28 | — |
| 332 | 0 | 0 | 0 | — | 0 | 0 | — | — | 56 | 0 |
| 339 | 0 | 0 | 0 | 0 | 0 | 3 | — | 0 | — | — |
| Total No. of Parasites Remaining | 1 | 0 | 0 | 0 | 0 | 3 | 3 | 0 | 154 | 0 |
| Average No. of Parasites Remaining | <1 | 0 | 0 | 0 | 0 | <1 | 1.5 | 0 | 39 | 0 |
| %Efficacy | 99.9 | 100 | 100 | 100 | 100 | 90.6 | 96.0 | 100 | 0 | positive (100) |

— = no infection (or very light infection).
0 = parasitism detected as indicated by EPG data, but no parasites recovered.

From an evaluation of the foregoing tests results, it is concluded that the new benzoyl chloride phenylhydrazones of this invention, particularly (alkyl)benzoyl chloride phenylhydrazones and benzoyl chloride phenylhydrazones according to Formula 1, and more particularly p-toluoyl chloride phenylhydrazone and benzoyl chloride phenylhydrazone, itself, are efficacious anthelmintic agents.

In the foregoing tests, the new compound p-toluoyl chloride phenylhydrazone and benzoyl chloride phenylhydrazone were administered orally as a finely divided solid (a powder) in a gelatin capsule. This uncomplicated form and route of administration is convenient for the compounds of this invention because they are solids at room temperature and they are not very soluble (almost insoluble) in water. A single dose was administered, but multiple doses can be used.

Other forms and routes of administration, and other formulations of the active ingredient are contemplated as embodiments of this invention. For example, aqueous or oil suspensions can be administered orally, or the compounds can be formulated with a solid carrier for feeding. Furthermore, an oil suspension can be converted into an aqueous emulsion by mixing with water and injecting the emulsion intramuscularly, subcutaneously or into the peritoneal cavity.

Pure compounds, mixtures of the active compounds, or combinations thereof with a solid carrier can be administered in the animal's food, or administered in the form of tablets, pills, boluses, wafers, and other conventional unit dosage forms. All of these various forms of the active compounds of this invention can be prepared using physiolgically acceptable carriers and known method of formulation and manufacture.

Representative solid carriers conveniently available and satisfactory for physiologically acceptable, unit dosage formulations include corn starch, powdered lactose, powdered sucrose, talc, stearic acid, magnesium stearate, finely divided bentonite, and the like. The active agent can be mixed with a carrier in varying proportions from, for example, about 0.001 percent by weight in animal food to about 90 or 95 percent or more in a pill or capsule. In the latter form, one might use no more carrier than sufficient to bind the particles of active compound.

The compounds of this invention should be mixed with animal feeds, in a way that will avoid degradation of the compound. The chlorine atom in the benzoyl chloride is substantially reactive, and amino groups and enzymes present in a feed might promote degradation. Certain kinds of animal feeds such as whole oats will give no problem, but others such as ground feed mixes can. Accordingly, administration to animals via their feed will require some information, judgment, and evaluation.

In general, the compounds can be formulated in stable powders or granules for mixing in an amount of feed for a single feeding or enough feed for one day and thus obtain therapeutic efficacy without complication. It is the prepared and stored feeds or feed premixes that require care. A recommended practice is to coat a granular formulation to protect and preserve the active ingredient. A prepared hog-feed containing about 0.2 percent of the active compound will provide a dosage of about 100 mg. per kg. body weight for each 100 lb. pig in its daily ration.

A solid diluent carrier need not be homogeneous entity, but mixtures of different diluent carriers can be used. Moreover, formulations with a solid carrier can include small proportions of adjuvants such as water; alcohols; protein solutions and suspensions like skimmed milk; edible oils; sugar solutions, e.g. syrups; and organic adjuvants such as propylene glycols, sorbitol, glycerol, diethyl carbonate, and the like.

The solid carrier formulations of the invention are conveniently prepared in unit dosage forms, to facilitate administration to animals. Accordingly, a large bolus (about 20 g. weight of active compound) would be required for a single dosage to a 900 lb. horse at a dosage rate of 50 mg./kg. of body weight. Similarly, a 60 lb. lamb at a dosage rate of 100 mg./kg. of body weight would require a pill, capsule, or bolus containing about 2.7 g. of active compound. A small dog, on the other hand, weighing about 20 lbs., would require a total dosage of about 225 mg. at a dosage rate of 25 mg./kg. of body weight. The solid unit dosage forms can be conveniently prepared in various sizes and concentrations of active ingredient, to accommodate treatment of the various sizes of animals that are parasitized by worms.

Liquid formulations can also be used. Representative liquid formulations include aqueous (including isotonic saline) suspensions, oil solutions and suspensions, and oil in water emulsions. Aqueous suspensions are obtained by dispersing the active compound in water, preferably including a suitable surface-active dispersing agent such as a cationic, anionic, or non-ionic surface active agents. Representative suitable ones are polyoxyalkylene derivatives of fatty alcohols and of sorbitan esters, and glycerol and sorbitan esters of fatty acids. Various dispersing or suspending agents can be included and representative ones are synthetic and natural gums, tragacanth, acacia, alginate, dextran, gelatin, methylcellulose, polyvinylpyrrolidone, and the like. The proportion of the active compound in the aqueous suspensions of the invention can vary from about 1 percent to about 20 percent or more.

Oil solutions are prepared by mixing the active compound and an oil, e.g., an edible oil such as cottonseed oil, peanut oil, coconut oil, modified soybean oil, and sesame oil. Usually, solubility in oil will be limited and oil suspensions can be prepared by mixing additional finely divided compound in the oil.

Oil in water emulsions are prepared by mixing and dispersing an oil solution or suspension of the active compound in water preferably aided by surface-active agents and dispersing or suspending agents as indicated above.

In general, the formulations of this invention are administered to animals so as to achieve therapeutic or prophylactic levels of the active compound. At present, it is known that 100 mg./kg. of body weight in lambs will effectively combat a wide variety of parasitic worms. Much lower effective dosages are contemplated, e.g., in the range of 25 to 75 mg./kg. of body weight.

In other animals, and for other kinds of parasitic worms, definitive dosages can be proposed. Contemplated are dosage rates of about 1 mg. to about 800 mg. per kg. of body weight. A preferred, contemplated range of dosage rates is from about 5 mg. to about 400 mg. per kg. of body weight. In this regard, it should be noted that the concentration of active compound in the formulation selected for administration is in many situations not critical. One can administer a larger quantity of a formulation having a relatively low concentration and achieve the same therapeutic or prophylactic dosage as a relatively small quantity of a relatively more concentrated formulation. More frequent small dosages will likewise give results comparable to one large dose. Unit dosage forms in accordance with this invention can have anywhere from less than 1 mg. to 500 g. of active compound per unit.

If desired the solid unit dosage forms of this invention including pellets and granules can be coated so as to provide timed released in the digestive system of animals. Such laminated or enteric coated forms are prepared by appropriately applying to a pill or bolus a polymeric acid or a mixture of a polymeric acid with shellac. and cetyl alcohol, cellulose acetate, or styrene maleic acid copolymer.

EXAMPLE 32

Following the procedure of Example 31, above, but substituting p-nitrobenzoyl chloride phenylhydrazone. 3,4-dichlorobenzoyl chloride phenylhydrazone, benzoyl chloride (2,5-dichlorophenyl)hydrazone, p-fluorobenzoyl chloride phenylhydrazone, p-chlorobenzoyl chloride (p-bromophenyl)hydrazone.
p-chlorobenzoyl chloride (2,4,6-trichlorophenyl)hydrazone,
benzoyl chloride (2,4,6-trichlorophenyl)hydrazone,
m-chlorobenzoyl chloride phenylhydrazone,
p-isopropylbenzoyl chloride phenylhydrazone,
o-toluoyl chloride phenylhydrazone,
2,4-dichlorobenzoyl chloride phenylhydrazone,
o-chlorobenzoyl chloride phenylhydrazone,
benzoyl chloride o-tolylhydrazone,
m-toluoyl chloride phenylhydrazone,
benzoyl chloride (p-chlorophenyl)hydrazone,
p-bromobenzoyl chloride phenylhydrazone,
benzoyl chloride (p-nitrophenyl)hydrazone,
benzoyl chloride (2,4-dibromophenyl)hydrazone,
2,5-dimethylbenzoyl chloride phenylhydrazone,
2-chloro-4-nitrobenzoyl chloride phenylhydrazone,
2,6-dichlorobenzoyl chloride phenylhydrazone,
pentafluorobenzoyl chloride phenylhydrazone,
3,4-dimethylbenzoyl chloride phenylhydrazone,
p-idobenzoyl chloride phenylhydrazone,
3-methyl-4-nitrobenzoyl chloride phenylhydrazone,
3,5-dimethylbenzoyl chloride phenylhydrazone,
p-butylbenzoyl chloride phenylhydrazone,
p-(1-methylbutyl)benzoyl chloride phenylhydrazone,
p-hexylbenzoyl chloride phenylhydrazone,
3,4,5-trimethylbenzoyl chloride phenylhydrazone,
2,4,6-triisopropylbenzoyl chloride (3,5-diisopropylphenyl)hydrazone,
p-toluoyl chloride (p-ethylphenyl)hydrazone,
p-hexylbenzoyl chloride (p-hexylphenyl)hydrazone,
3-chloro-5-methylbenzoyl chloride phenylhydrazone,
p-toluoyl chloride (p-bromophenyl)hydrazone,
p-nitrobenzoyl chloride (-bromophenyl)hydrazone, p-nitrobenzoyl chloride (p-isopropylphenyl)hydrazone, p-isopropylbenzoyl chloride (2-chloro-4-nitrophenyl)hydrazone, and benzoyl chloride (2,4-dichlorophenyl)hydrazone for p-toluoyl chloride phenylhydrazone, similar efficacies against parasitic helminths are obtained.

I claim:

1. A method of controlling parasitic worms in animals which comprises administering orally or parenterally to an animal a therapeutic or prophylactic dosage of a benzoyl chloride phenylhydrazone having the structural formula:

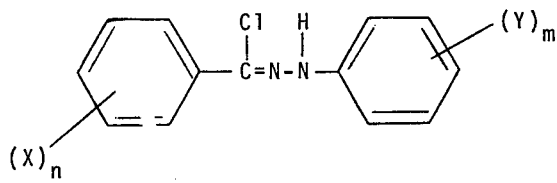

wherein X is halogen, alkyl of from 1 to 6 carbon atoms, inclusive, and nitro; Y is halogen, alkyl of from 1 to 6 carbon atoms, inclusive, and nitro; $n$ is an integer from 0 to 5, inclusive; and m is an integer from 0 to 3, inclusive; the sum of $n+m$ being not more than 6, the sum of carbon atoms in alkyl substituents being not more than 15, and there being no more than one nitro group in the molecule.

2. The method according to claim 1 wherein the compound p-toluoyl chloride phenylhydrazone is administered.

3. The method according to claim 1 wherein the compound benzoyl chloride phenylhydrazone is administered.

4. The method according to claim 1 wherein X is alkyl of 1 to 6 carbon atoms, inclusive.

5. The method according to claim 4 wherein $n$ is 1.

6. The method according to claim 5 wherein $m$ is 0.

7. The method according to claim 6 wherein the alkyl group is methyl.

8. The method according to claim 1 wherein $n$ is 1.

9. The method according to claim 8 wherein $m$ is 0.

* * * * *

UNITED STATES PATENT AND TRADEMARK OFFICE
CERTIFICATE OF CORRECTION

PATENT NO. : 3,932,661

DATED : January 13, 1976

INVENTOR(S) : Girts Kaugars

Page 1 of 2

It is certified that error appears in the above—identified patent and that said Letters Patent is hereby corrected as shown below:

Column 3, line 24: "alliphatic" should read -- aliphatic --.
Column 3, line 28: "bezene," should read -- benzene, --.
Column 3, line 57: "metthods" should read -- methods --.
Column 7, line 2: "12.28" should read -- 12.38 --.
Column 10, line 66: "45°3C." should read -- 45° C. --.
Column 12, line 35: "o-tolyhydrazide" should read -- o-tolylhydrazide --.
Column 14, line 3: "H, 293;" should read -- H, 2.93; --.
Column 14, line 49: "above for" should read -- above) for --.
Column 16, line 35: "compounds" should read -- components --.
Column 18, line 44: "waterimmiscible" should read -- water-immiscible --.
Column 20, line 17: "Epilachna" should read -- (Epilachna --.
Column 20, line 18: "donestica" should read -- domestica --.
Column 20, line 38: "(2,5dichlorophenyl)" should read -- (2,5-dichlorophenyl) --
Column 21, line 35: "subsequent. similar," should read -- subsequent, similar, --.
Column 22, line 2: "anthelimintic" should read -- anthelmintic --.
Columns 21-22, TABLE: "Haemon-   Oesopha-   Bunos-"
                              gostomun
                     chus                 tomum should read -- Haemonchus   Oesopha-   Bunostomum   --.
                            gostomum

UNITED STATES PATENT AND TRADEMARK OFFICE
CERTIFICATE OF CORRECTION

PATENT NO. : 3,932,661

DATED : January 13, 1976

INVENTOR(S) : Girts Kaugars

It is certified that error appears in the above—identified patent and that said Letters Patent is hereby corrected as shown below:

Columns 23-24, Table:

"Haemon-  Oesopha-  Bunos-" should read --   Haemonchus  Oesopha-  Bunostomum --
 chus     gos-                                            gostomum
          tomum     tomum Columns 23-24, Table:

"Haemon-  Oesopha-  Bunos-" should read --  Haemonchus  Oesopha-   Bunostomum --
 chus     gos-                                          gostomum
          tomum     tomum Column 24, line 45: "physiolgically" should read -- physiologically --.
Column 26, line 24: "shellac. and" should read -- shellac, and --.
Column 26, line 35: "hydrazone." should read -- hydrazone, --.
Column 26, line 55: "p-idobenzoyl" should read -- p-iodobenzoyl --.
Column 26, line 69: "(-bromophenyl)" should read -- (p-bromophenyl) --.

Signed and Sealed this

Eighth Day of September 1981

[SEAL]

Attest:

GERALD J. MOSSINGHOFF

Attesting Officer    Commissioner of Patents and Trademarks